(12) United States Patent
Masada et al.

(10) Patent No.: US 7,605,124 B2
(45) Date of Patent: Oct. 20, 2009

(54) EJECTION LIQUID AND EJECTION METHOD

(75) Inventors: Yohei Masada, Kawasaki (JP); Masaru Sugita, Tokyo (JP); Hideki Kaneko, Yokohama (JP); Naoko Sakurada, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/746,305

(22) Filed: May 9, 2007

(65) Prior Publication Data

US 2007/0206081 A1 Sep. 6, 2007

Related U.S. Application Data

(63) Continuation-in-part of application No. 11/570,744, filed as application No. PCT/JP2005/018247 on Sep. 27, 2005.

(30) Foreign Application Priority Data

| Sep. 27, 2004 | (JP) | ............................ 2004-279864 |
| Aug. 31, 2005 | (JP) | ............................ 2005-252154 |
| Jan. 9, 2007 | (JP) | ............................ 2007-001179 |

(51) Int. Cl.
*A61K 38/28* (2006.01)
*A61K 31/19* (2006.01)
*A01N 37/00* (2006.01)

(52) U.S. Cl. ............................ 514/3; 514/557; 514/866
(58) Field of Classification Search ........................ None
See application file for complete search history.

(56) References Cited

U.S. PATENT DOCUMENTS

| 4,371,523 | A | * | 2/1983 | Grodsky et al. .................. 514/3 |
| 4,476,118 | A | * | 10/1984 | Brange et al. .................... 514/3 |
| 5,894,841 | A | | 4/1999 | Voges ..................... 128/203.12 |
| 6,120,761 | A | | 9/2000 | Yamazaki et al. ........... 424/85.1 |
| 6,277,367 | B1 | | 8/2001 | Yamazaki et al. ........... 424/85.1 |
| 6,525,102 | B1 | | 2/2003 | Chen et al. .................... 514/970 |
| 6,548,020 | B2 | | 4/2003 | Okamoto et al. ............. 422/68.1 |
| 6,569,406 | B2 | | 5/2003 | Stevenson et al. ............... 424/43 |
| 6,627,187 | B2 | | 9/2003 | Yamazaki et al. ........... 424/85.1 |
| 6,838,975 | B2 | | 1/2005 | Litwiller et al. ............. 340/5.67 |
| 6,921,433 | B2 | | 7/2005 | Kuribayashi et al. ......... 106/499 |
| 6,926,392 | B2 | | 8/2005 | Sasaki et al. .................... 347/65 |
| 6,964,700 | B2 | | 11/2005 | Uji et al. ................... 106/31.28 |
| 7,011,825 | B2 | | 3/2006 | Yamazaki et al. ........... 424/85.1 |
| 7,030,086 | B2 | | 4/2006 | Chen et al. .................... 514/12 |
| 7,083,667 | B2 | | 8/2006 | Murai et al. ............... 106/31.43 |
| 7,202,065 | B2 | | 4/2007 | Römisch et al. ............. 435/183 |
| 2002/0092519 | A1 | | 7/2002 | Davis .................... 128/200.14 |
| 2002/0110552 | A1 | | 8/2002 | Römisch et al. ........... 424/94.63 |
| 2002/0177221 | A1 | | 11/2002 | Nishiguchi et al. ....... 435/287.2 |
| 2003/0119179 | A1 | | 6/2003 | Okamoto et al. ......... 435/287.2 |
| 2003/0190316 | A1 | | 10/2003 | Kakuta et al. ............. 424/132.1 |
| 2004/0037803 | A1 | | 2/2004 | Sato .......................... 424/85.1 |
| 2004/0259083 | A1 | | 12/2004 | Oshima .......................... 435/6 |
| 2005/0188894 | A1 | | 9/2005 | Yamagishi et al. ........ 106/31.43 |
| 2006/0093576 | A1 | | 5/2006 | Chen et al. .................. 424/85.2 |
| 2006/0093598 | A1 | | 5/2006 | Chen et al. .................. 424/94.2 |
| 2006/0183046 | A1 | | 8/2006 | Murai et al. ............... 430/108.2 |
| 2007/0221215 | A1 | | 9/2007 | Sugita et al. ........... 128/203.12 |
| 2007/0277701 | A1 | | 12/2007 | Toyoda et al. ............ 106/31.48 |

FOREIGN PATENT DOCUMENTS

| EP | 1 314 437 A1 | 5/2003 |
| JP | 04041421 * | 2/1992 |
| JP | 7-173073 A | 7/1995 |
| JP | 2002/248171 A | 9/2002 |
| JP | 2002-249441 A | 9/2002 |
| JP | 2002/355025 A | 12/2002 |
| JP | 2003/510368 A | 3/2003 |
| JP | 2003/154655 A | 5/2003 |
| JP | 2003/154665 A | 5/2003 |
| JP | 2004-515467 | 5/2004 |
| JP | 2004-196824 A | 7/2004 |
| JP | 3610231 | 1/2005 |
| JP | 3618633 | 2/2005 |
| WO | WO 01/24814 A1 | 4/2001 |
| WO | WO 02/11695 A2 | 2/2002 |
| WO | WO 02/13860 A1 | 2/2002 |
| WO | WO 02/17957 A1 | 3/2002 |
| WO | WO 02/092813 A1 | 11/2002 |
| WO | WO 02/094342 A2 | 11/2002 |

OTHER PUBLICATIONS

English language abstract DERWENT-ACC-No. 1992-099821; 3 pages.*
Watanabe et al. (Abstract: Zoological Science 2003, 20, 429-434) 1 page.*
Goodall et al. (Abstract: J Aerosol Med 2002 1593) 351-357). 1 page.*
Todo et al. (International Journal of Pharmaceutics 2004, 271, 41-52).*

(Continued)

*Primary Examiner*—Ernst V Arnold
(74) *Attorney, Agent, or Firm*—Fitzpatrick, Cella, Harper & Scinto

(57) ABSTRACT

An ejection liquid that allows a solution containing at least one kind of insulins to be stably ejected by an inkjet system using a thermal energy and a method of ejecting the solution containing at least one kind of insulins, using such an ejection liquid. The ejection liquid of the present invention includes at least one kind of insulins, citric acid, and a liquid medium, which can be ejected by providing thermal energy.

7 Claims, 3 Drawing Sheets

OTHER PUBLICATIONS

Figure 1:
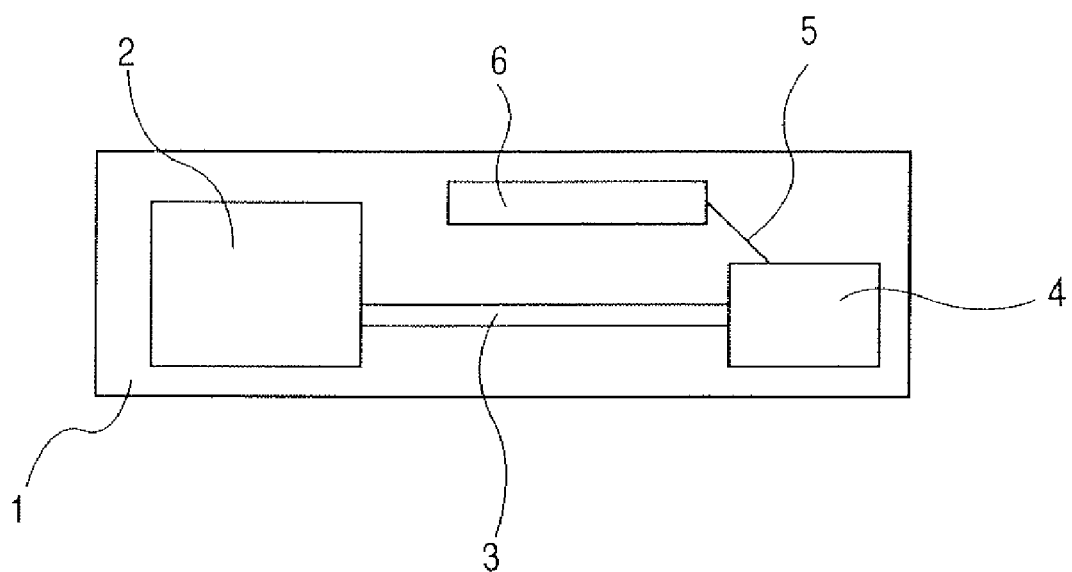
Figure 2:
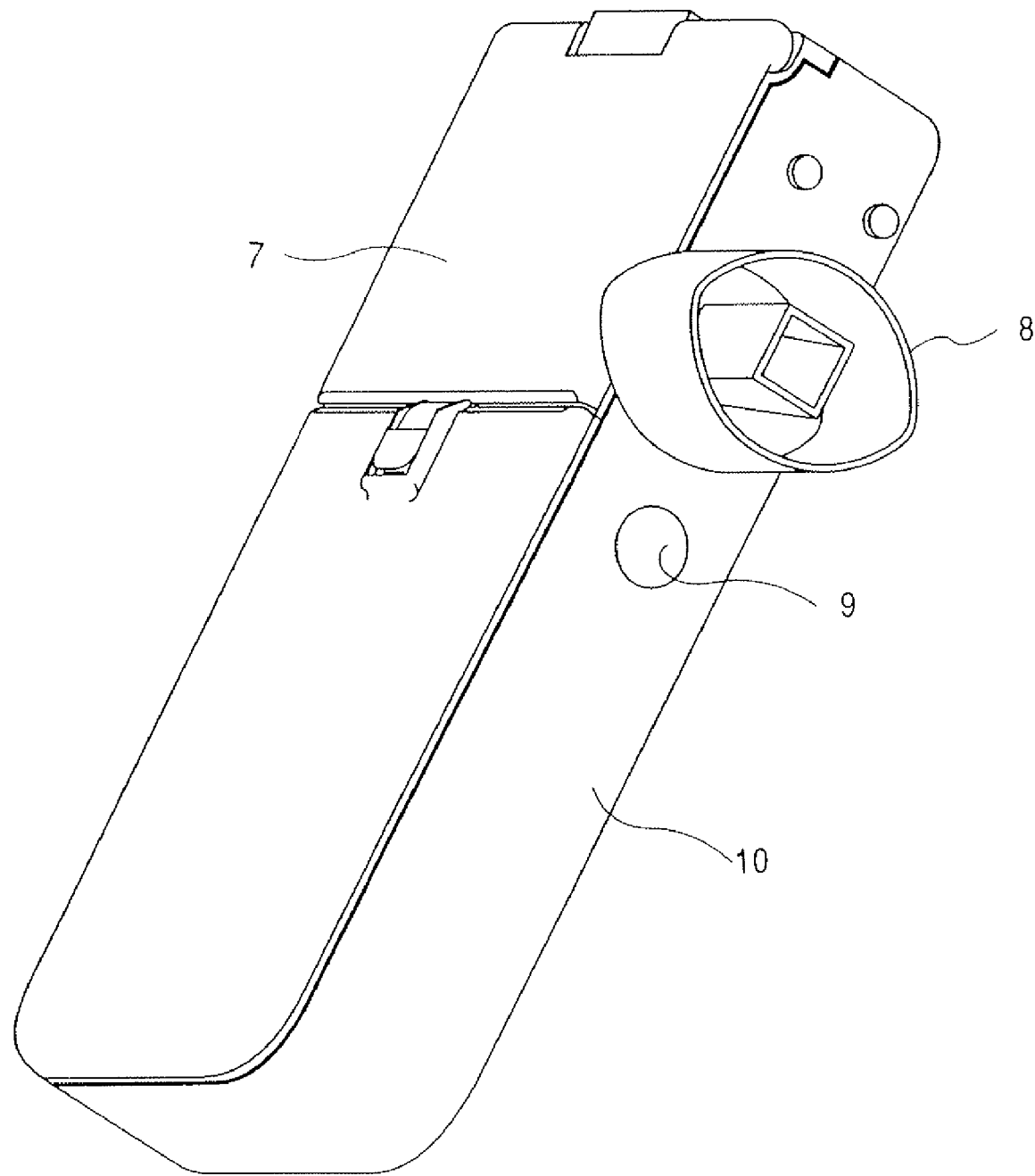
Figure 3:
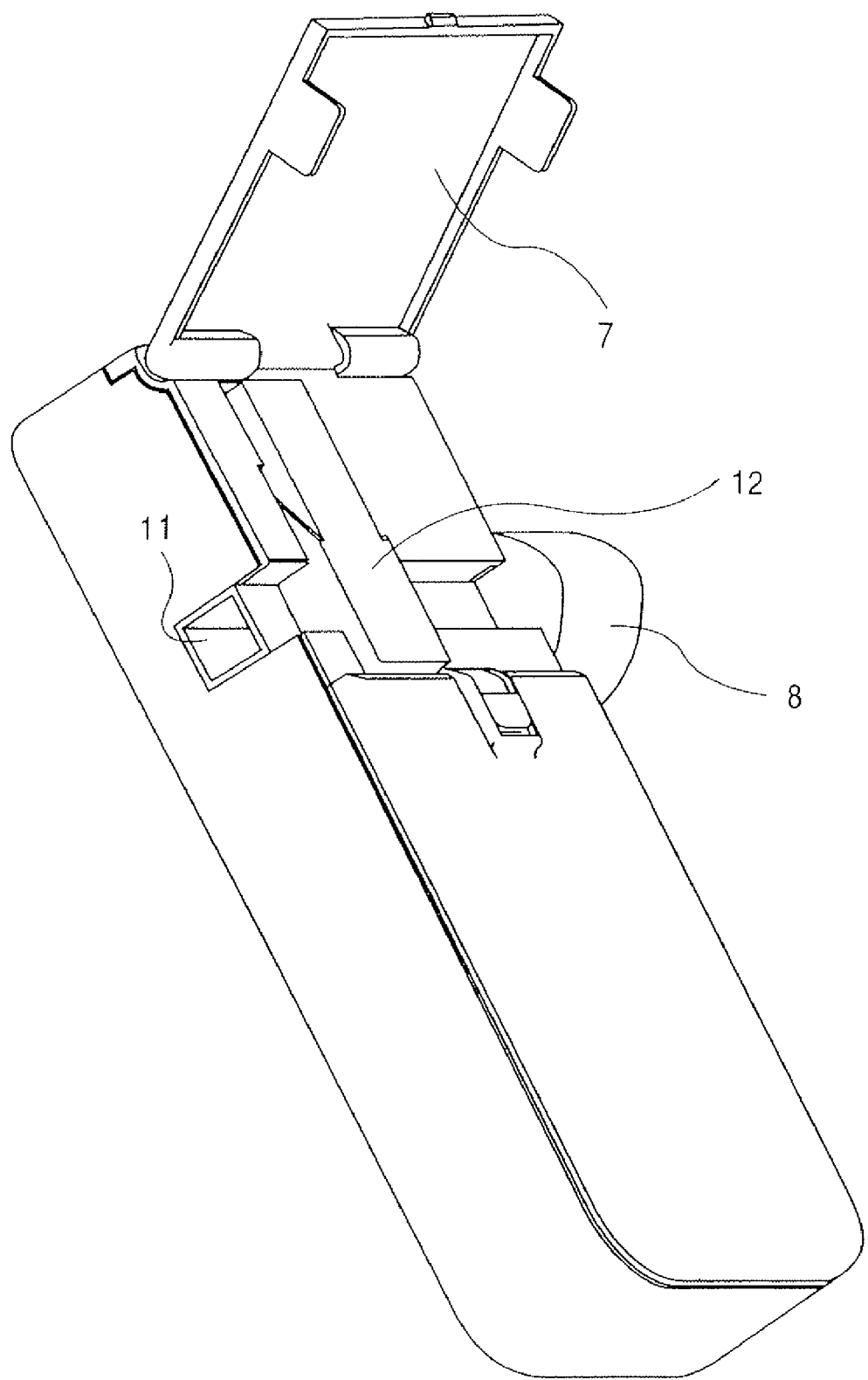

Allain et al., "Microarray sampling-platform fabrication using bubble-jet technology for a biochip system," Fresenius J. Anal. Chem., vol. 371, 2001, pp. 146-150.

Howard et al., "Ink-Jet Printer Heads for Ultra-Small-Drop Protein Crystallography," BioTechniques, vol. 33, No. 6, Dec. 2002, pp. 1302-1306.

Critical Reviews in Therapeutic Drug Carrier Systems, 12 (2 & 3) (1995), pp. 233-261.

Mar. 26, 2008 Japanese Official Action in Japanese Patent Appln. No. 2005-252154 (with translation).

Motonori Kudo, et al., "Control of Suppression/Promotion of Aggregation by Addition of Small Molecule", Summary Collection of Japan Society for Bioscience, Biotechnology and Agrochemistry Convention, 2002, vol. 2002, 216.

Kentaro Shiraki, "Small Molecule Additive for Suppressing Deactivation and Agglomeration of Protein", Biophysics, 2004, vol. 44, No. 2, pp. 87-90.

* cited by examiner

EJECTION LIQUID AND EJECTION METHOD

CROSS-REFERENCE TO RELATED APPLICATION

This is a continuation-in-part application of U.S. patent application Ser. No. 11/570,744, filed on Dec. 15, 2006, which is a national stage of PCT/JP2005/018247 filed Sep. 27, 2005 and claims benefit of Japanese Patent Application Nos. 2004-279864, filed Sep. 27, 2004 and 2005-252154 filed Aug. 31, 2005.

BACKGROUND OF THE INVENTION

1. Field of the Invention

The present invention relates to a liquid composition suitable for ejecting a liquid containing at least one kind of insulins and to a method of ejecting the liquid.

2. Related Background Art

Currently, many attempts have been conducted to utilize a protein solution as liquid droplets. Examples thereof include transmucosal administration for the drug delivery method or an application of liquid droplets forming technique using the protein solution to a biochip or biosensor in which an extremely small amount of a protein is required. In addition, attentions have been paid on a method of using microdroplets of protein for control on crystallization of protein and also for screening of a physiologically active substance (see, for example, Japanese Patent Application Laid-Open No. 2002-355025, Allain L R et al., "Fresenius J. Anal. Chem.", vol. 371, p. 146-150, 2001, and Howard E I and Cachau R E, "Biotechniques", vol. 33, p. 1302-1306, 2002).

In recent years, mass production of proteins, particularly of useful proteins such as enzymes and those having physiological activities has become possible by any technology such as genetic recombinant technology. Therefore, the process of making protein into liquid droplets can be a useful means in the field of searching, utilizing, and applying a novel protein medicine. More specifically, there are increasing significant demands on means for providing patients with various pharmaceutical agents by microdroplets. In particular, microdroplets have become important means for the administration of proteins, peptides, and other biological materials from the lungs. In other words, pulmonary administration has been remarked as an administration route in place of an injection of a macromolecule peptide-based drug represented by insulin because the lungs have air vesicles with their own extensive surface areas of 50 to 140 $m^2$ and the epithelium provided as a barrier of absorption is as thin as 0.1 μm, while the enzyme activities of the lungs are smaller than those of the gastrointestinal tract.

Among the macromolecular peptide drugs which can be administered through the lungs, much attention has been paid on insulins. The patient with type I diabetes cannot produce insulin in the body and requires the administration of insulins before a meal. Examples of the insulins include normal insulins, rapidly-acting insulin aspart, insulin lispro, long-acting insulin glargine, and insulin detemir. The administration of insulins by injection before every meal may result in pain and infection, so the pulmonary administration of insulins without such concerns has attracted attention.

In general, the deposition of microdroplets of drug in the lungs has been known to depend largely on the aerodynamic particle sizes thereof. In particular, the delivery of the microdroplets to the air vesicles in the deep portions of the lungs requires an administration with high reproducibility for the liquid droplets having particle sizes of 1 to 5 μm and having a narrow particle size distribution.

As a method of preparing liquid droplets with a narrow particle size distribution, the use of a droplet generator diverted from those used in inkjet printing based on the principle of a liquid ejection in the production of extremely fine liquid droplets and the application of the liquid droplets have been reported in the art (see, for example, U.S. Pat. No. 5,894,841 and Japanese Patent Application Laid-Open No. 2002-248171). Here, the liquid ejection by the specific inkjet system concerned involves leading a liquid to be ejected into a small chamber where the liquid is subjected to a physical stress, thereby allowing liquid droplets of the liquid to be ejected from orifices. An ejecting method may be any one of those known in the art, such as a method that involves generating air bubbles spouting liquid droplets through orifices (ejection opening) formed on a chamber by means of an electrothermal conversion element such as a thin-film resistor (i.e., a thermal inkjet system) and a method that involves ejection liquid directly from orifices formed on a chamber by means of a piezoelectric transducer (i.e., a piezo inkjet method).

For allowing the lungs to absorb a drug, in particular, in a case of insulins, for example, the dose of the drug should be controlled precisely. Therefore, making liquid droplets based on the principle of the inkjet system, which is capable of adjusting the ejection amount thereof, is a very preferable configuration. However, the ejection of a solution should be surely carried out in this case, the ejection of the solution of insulins is unstable when the solution is only controlled with respect to its surface tension and viscosity. Therefore, there has often been difficulty in ejection with high reproducibility and high efficiency.

A problem accompanying the formation of liquid droplets from an insulins solution based on the principle of the inkjet system is to make the structure of insulins unstable by physical force, such as pressure or shearing force, to be applied when the liquid droplets are ejected or by high surface energy which is characteristic of fine liquid droplets. In addition to this, when a thermal inkjet system is used, thermal energy is also added. The conformation of insulins are fragile. Thus, when the conformation is destroyed, the aggregation and degradation of insulins may be caused and affect the normal ejection. The physical actions are extremely larger than the shearing force and thermal energy to be applied by conventional stirring or heat treatment (for example, in the case of the thermal inkjet system, approximately 300° C. and 90 atm are applied momentarily). In addition, several physical stresses are impressed at the same time, so the stability of the insulins may tend to be substantially lowered, compared with the case of usually handling the insulins. If such a problem occurs, the insulins may be aggregated at the time of making liquid droplets and nozzles may be then clogged, thereby making it difficult to eject liquid droplets.

Further, liquid droplets having diameters of 1 to 5 μm, which are suitable for the inhalation into the lungs, are extremely much smaller than those having diameters of approximately 16 μm generally used in any printer commercially available at present. Therefore, a larger surface energy or shearing stress may be impressed on the liquid droplets than on the liquid droplets used in the printer. Therefore, it is much more difficult to eject microdroplets suitable for inhalation of the insulins into the lungs.

In addition, the present inventors have studied and found out that the insulins solution can be unstably ejected as the drive frequency of a thermal inkjet head increases. This is because part of the insulins can be insoluble in water when the liquid to be ejected is heated by a heater in the thermal inkjet head and the heater can be prevented from transferring energy to the liquid. When the drive frequency is low, even though an insoluble matter is temporarily generated, it can be re-dissolved within a time period before the next driving. On the other hand, when the drive frequency increases, the stability of ejection may decrease due to insufficient recovery from the dissolution. However, a low drive frequency leads to a decrease in amount of the liquid which can be ejected per unit time, so the ejection should be carried out at an adequately high frequency in actual use.

Therefore, it is essential to develop an ejection liquid that allows a stable ejection of insulins in actual use.

In contrast, as a method of stabilizing insulins, a method of adding a surfactant, glycerol, any of various kinds of carbohydrates, a water-soluble polymer such as polyethylene glycol, or albumin has been known in the art. However an improvement in ejection stability when insulins are ejected on the basis of a thermal inkjet system is hardly attained or is not attained.

In addition, there is substantially no effect on an improvement in ejection performance when a solution of insulins is ejected even after formulation with polyols such as ethylene glycol and glycerin, and a moisturizing agent such as urea, which are suitable additives for ink to be used in inkjet printing.

For the liquid composition of insulins for use in pulmonary inhalation of liquid droplets produced by using the thermal inkjet system, there have been known liquid compositions which contain compounds for controlling surface tension and humectants (see International Publication No. WO 02/094342). In this case, a surfactant and a water-soluble polymer such as polyethylene glycol are added to improve the stability of a protein and a peptide as shown an insulin in a solution formed into liquid droplets by modifying the surface tension, viscosity, and moisturizing activity of the solution.

However, no detailed description about ejection stability is given in the International Publication No. WO 02/094342. Further, according to the investigation of the present inventors, it has been found that the effect of the addition of a surfactant and a water-soluble polymer is insufficient when the concentrations of the protein and the peptide are high. Further, it has also been found that most of the surfactants have no effect, and that the ejection stability of a protein solution is not determined by its surface tension, viscosity, and moisturizing action. In other words, the aforementioned method is not a general method of stabilizing the ejection when insulins are ejected by the thermal inkjet system.

SUMMARY OF THE INVENTION

The present invention is based on the finding of a composition having a higher ejection stability compared with that of the conventional ejection liquid. In other words, it is an object of the present invention to provide an ejection liquid (liquid composition) for stably ejecting a solution containing at least one kind of insulins using thermal energy and to provide an ejection method suitable for the ejection of such an ejection liquid.

According to the present invention, there is provided an ejection liquid, which can be ejected by an application of thermal energy, including: at least one kind selected from insulins; citric acid; and a liquid medium.

Further, according to the present invention, there is provided a liquid ejection cartridge, including: a tank in which the ejection liquid is stored; and an ejection head having an electrothermal conversion element providing the ejection liquid with a thermal energy.

Still further, according to the present invention, these is provided an inhaler, including: the above cartridge; and an ejection orifice for introducing the liquid ejected from a liquid ejection part in an ejection head of the cartridge into an inhalation part of a user.

Yet further, according to the present invention, there is provided a method of ejecting a liquid containing at least one kind of insulins by providing the liquid with a thermal energy, in which the liquid contains citric acid.

Yet further, according to the present invention, citric acid is added to the solution containing at least one kind of insulins, whereby an ejection liquid capable of being ejected stably based on the inkjet system can be prepared. The ejection liquid may be provided as liquid droplets by ejecting from a portable ejection device, and it is inhaled, so at least one kind of the insulins can be transferred to the lungs and can be absorbed in the body. In addition, in the above-mentioned method, the ejection liquid can be used for the production of a biochip and biosensor, and the like by ejecting it on a substrate.

Further features of the present invention will become apparent from the following description of exemplary embodiments with reference to the attached drawings.

BRIEF DESCRIPTION OF THE DRAWINGS

FIG. 1 is a perspective view illustrating a liquid ejection cartridge unit for an inhaler.

FIG. 2 is a schematic view illustrating an inhaler used in the present invention.

FIG. 3 is a schematic view illustrating a state in which an access cover of the inhaler of FIG. 2 is opened.

DESCRIPTION OF THE EMBODIMENTS

Preferred embodiments of the present invention will now be described in detail in accordance with the accompanying drawings.

The term "insulins" herein used refers to insulin and any polypeptide dissolved or dispersed in an aqueous solution in which the amino acid sequence of insulin is partially modified. Such insulins may be chemically synthesized or may be obtained by the recombination of a natural product purified from a natural source. The effects of insulins may be improved, for example, by the chemical modification of insulin with a covalent bond to an amino acid residue of insulin to thereby prolong their therapeutic effects.

For carrying out the present invention, various insulins which are allowed to form liquid droplet can be used. Insulins to be used in the present invention are not particularly limited as long as they have a physiologically activity to a living body and an activity in a living body. The most typical of the formation of liquid droplets from insulins in the present invention are suitably available for delivering therapeutically-effective insulins to the lungs.

Examples of insulins include insulin, products thereof with modified amino acid sequences such as insulin aspart, insulin lispro, insulin glargine, and insulin detemir. In addition, any peptide portion of the insulins, which has the whole or part of the main structure of the above substance and at least part of biological characteristics of insulin, can be also used. Any of substances as described above, which is modified with a water-soluble polymer such as PEG or PVA, can be also used.

The fact that proteins and peptides modified with PEG and PVA can be delivered to the lungs is explicitly disclosed in Critical Reviews in Therapeutic Drug Carrier Systems, 12 (2 & 3) (1995).

Further, for the application of any of insulins to the production of a biochip, a biosensor, or the like, the above substance modified with a reagent for immobilizing insulins, such as 4-azidobenzoic acid N-hydroxysuccinimide ester, may be used.

The content of at least one selected from insulins in an ejection liquid is preferably 1 μg/ml to 200 mg/ml, more preferably 0.1 mg/ml to 60 mg/ml, depending on the purpose, use, or kind thereof.

In addition, the most prominent improvement of ejection property can be attained when a thermal inkjet system is applied on the present invention, so the following description will be made on the basis of the principle of the thermal inkjet system. In the present invention, however, a piezo inkjet system where a liquid is ejected from a nozzle with the vibratory pressure of a piezoelectric element may be alternatively employed. The ejection system may be chosen depending on the kind of a protein or a peptide to be ejected.

When the thermal inkjet system is employed, the size of an orifice, the heat capacity of a thermal pulse to be used for ejection, and the size of a micro heater used therefor can be designed with higher precision and reproducibility. Therefore, the diameters of liquid droplets can be narrowed more than usual. Further, the head can be produced at low cost and with high adaptability to a small-sized device that requires frequent replacement of the head. Therefore, when the liquid ejection device requires portability and convenience, particularly, an ejection device of a thermal inkjet system is preferable.

For an improvement in ejection property of ink with an inkjet system, in general, the addition of a surfactant, ethylene glycol have been known in the art. However, for ejecting a solution containing at least one kind of insulins, the addition of those materials only does not attain an improvement in ejection property. Thus, an additional additive has been demanded.

The present inventors have investigated and confirmed that when the thermal inkjet system is used for the ejection without any additive while insulins are at concentrations enough to exert effective physiological activities, the ejection can hardly occur at an ejection frequency of 10 kHz or more.

As a result of intensive studies, the present inventors have found that the addition of citric acid as an effective component into a solution that contains at least one kind of insulins leads to a stable ejection due to the principle of an inkjet system using thermal energy.

A cause of which the addition of citric acid largely contributes to stability in ejection of an insulins solution has not been clear but it can be considered as follows: citric acid dissolves insulins at high concentration even in an insulins solution at a pH near the isoelectric point. Therefore, the high dissolving power of citric acid may quickly redissolve the insulins insolubilized by the load at ejection. The citric acid quickly redissolves the insolubles of insulins occurring to some extent in water. Thus, it is considered that the transfer of thermal energy to the solution is stabilized and thus the ejection can be also stabilized.

Citric acid may be added in the form of a salt, and thus alkali metal salt, such as those of sodium and potassium and ammonium salt, may be used.

In addition, the content of citric acid in the ejection liquid may be defined depending on the kinds and contents of insulins, but preferably is chosen from the range of 1 μg/ml to 2.0 g/ml, and more preferably is chosen from the range of 10 μg/ml to 200 mg/ml.

The liquid medium used preferably includes water or a water-based mixture liquid medium containing a water-soluble organic solvent. Specific examples of the water-soluble organic solvent include: amides, such as dimethylformamide and dimethylacetamide; ketones, such as acetone; ethers, such as tetrahydrofuran and dioxane; polyalkylene glycols, such as polyethylene glycol and polypropylene glycol; alkylene glycols, where an alkylene group has 2 to 6 carbon atoms, such as ethanol, ethyleneglycol, propylene glycol, butylene glycol, triethylene glycol, 1,2,6-hexane triol, thiodiglycol, hexylene glycol, and diethylene glycol; glycerin; lower alkyl ethers of polyalcohols, such as ethylene glycol monomethyl (or ethyl) ether, diethylene glycol monomethyl (or, ethyl) ether, and triethylene glycol monomethyl (or, ethyl) ether; and N-methyl-2-pyrrolidone.

In general, the content of the water-soluble organic solvent described above is preferably 0.1 to 40% by weight, and more preferably 1 to 30% by weight with respect to the total weight of the ejection liquid. In addition, the content of water in the liquid medium is in the range of 30 to 95% by weight. if the content of water is less than 30% by weight, it is not preferable because the solubility of protein deteriorates and the viscosity of the ejection liquid increases. In contrast, if it is higher than 95% by weight, the water evaporates excessively and a sufficient fixing property cannot be satisfied.

In the embodiments of the present invention, for improving the lung absorption efficiency of insulins, a surfactant may be used. Typical examples of the surfactant to be used include, but are not limited to: a sorbitan fatty acid ester such as sorbitan monocaprylate, sorbitan monolaurate, or sorbitan monopalmitate; an N-acylamino acid of a surfactant having an amino acid as a hydrophilic group, such as N-coconut oil fatty acid glycine, N-coconut oil fatty acid glutamic acid, or N-lauroyl glutamic acid; a fatty acid salt of an amino acid; a glycerin fatty acid ester such as glycerin monocaprylate, glycerin monomyristate, or glycerin monostearate; a polyglycerin fatty acid ester such as decaglyceryl monostearate, decaglyceryl distearate, or decaglyceryl monolinolate; a polyoxyethylene sorbitan fatty acid ester such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, or polyoxyethylene sorbitan tristearate; a polyoxyethylene sorbitan fatty acid ester such as polyoxyethylene sorbitol tetrastearate or polyoxyethylene sorbitol tetraoleate; a polyoxyethylene glycerin fatty acid ester such as polyoxyethylene glyceryl monostearate; a polyethylene glycol fatty acid ester such as polyethylene glycol distearate; a polyoxyethylene alkyl ether such as polyoxyethylene lauryl ether; a polyoxyethylene polyoxypropylene alkyl ether such as polyoxyethylene polyoxypropylene glycol ether, polyoxyethylene polyoxypropylene propyl ether, or polyoxyethylene polyoxypropylene cetyl ether; a polyoxyethylene alkylphenyl ether such as polyoxyethylene nonylphenyl ether; a polyoxyethylene hardened castor oil such as polyoxyethylene castor oil, polyoxyethylene hardened castor oil (polyoxyethylene hydrogenated castor oil); a polyoxyethylene beeswax derivative such as polyoxyethylene sorbitol beeswax; a polyoxyethylene lanolin derivative such as polyoxyethylene lanolin; a surfactant having HLB 6 to 18 such as a polyoxyethylene fatty acid amide (for example, polyoxyethylene stearamide); an anionic surfactant such as an alkyl sulfate having an alkyl group having 8 to 18 carbon atoms (for example, sodium cetyl sulfate, sodium lauryl sulfate, or sodium oleyl sulfate); a polyoxyethylene alkyl ether sulfate having the average number of additional moles of 2 to 4 of ethylene oxide and an alkyl group having 8 to 18 carbon atoms (for example, sodium polyoxyethylene lauryl sulfate); an alkyl benzene sulfonate having an alkyl group having 8 to 18 carbon atoms, such as sodium lauryl benzene sulfonate; an alkyl sulfosuccinate having an alkyl group having 8 to 18 carbon atoms, such as sodium lauryl sulfosuccinate; a natural surfactant such as lecithin or glycerophospholipid; a sphingophospholipid such as sphingomyelin; and a saccharose fatty acid ester of a fatty acid ester having 8 to 18 carbon atoms. Those surfactants can be added, alone or in combination with two kinds or more thereof, to an ejection liquid (liquid composition) of the present invention.

In the embodiments of the present invention, for removing microbial effects, an antimicrobial agent, a germicidal agent, and an antiseptic agent may be added. Examples of those agents include: quaternary ammonium salts such as benzalkonium chloride and benzatonium chloride; phenol derivatives such as phenol, cresol, and anisole; benzoic acids such as benzoic acid and paraoxybenzoic acid ester; and sorbic acid.

In the embodiments of the present invention, for elevating physical stability of an ejection liquid in conservation, any one of oil, glycerin, ethanol, urea, cellulose, polyethylene glycol, and alginate may be added. In addition, for elevating chemical stability, ascorbic acid, cyclodextrin, tocopherol, or any other anti-oxidizing agent may be added.

Any buffer or pH adjuster may be added to adjust the pH of the ejection liquid. Examples of the buffer or pH adjuster, which may be used, include ascorbic acid, diluted hydrochloric acid, and diluted sodium hydroxide, and also include other buffers such as sodium hydrogen phosphate, sodium dihydrogen phosphate, potassium hydrogen phosphate, potassium dihydrogen phosphate, PBS, HEPES, and Tris.

Aminoethylsulfonic acid, potassium chloride, sodium chloride, glycerin, or sodium hydrogen carbonate may be added as an isotonizing agent.

When the ejection liquid according to the present invention is used as a spray liquid, any one of saccharides such as glucose and sorbitol, sweetening agents such as aspartame, menthol, and various flavors may be added as a flavoring agent. Further, in addition to one having hydrophilic property, a hydrophobic compound, such as an oily compound may be used.

Further, various additives suitable for the usage of the ejection liquid, for example, surface regulators, viscosity regulators, solvents, moisturizers may be added in an appropriate amount, as needed. Specifically, hydrophilic binders, hydrophobic binders, hydrophilic thickeners, hydrophobic thickeners, glycol derivatives, alcohols, and electrolytes are examples of the available additives and may be used singly or in combination. Further, as the various substances described above to be used as additives, it is preferable to use those which are for medicinal use and listed in a national pharmacopoeia as subsidiary components that may be added in preparing therapeutic liquid formulations or those which are accepted to be utilized in foods and cosmetics.

The addition percentage of the various substances described above to be mixed as additives varies depending on the types of objective insulins, which is, in general, preferably within the range of 0.001 to 40% by weight, and more preferably within the range of 0.01 to 20% by weight. Further, the addition amount of the additives described above varies depending on the type, amount, and combination thereof, but, from the viewpoint of ejection property, it is preferable that the ratio be 0.1 to 100 parts by weight of the additive relative to 1 part by weight of the above-mentioned insulins.

For ejecting the insulins solution by a thermal inkjet system, the drive frequency of the head is preferably as low as possible. A difference in stability of ejection depending on the drive frequency may be due to the following reason: when an ejection liquid is heated by an electrothermal conversion element of a thermal inkjet head, it is considered that part of insulins comes to be insoluble in water and the electrothermal conversion element is prevented from transferring energy to the solution. When the drive frequency is low, even though an insoluble matter is temporarily generated, it can be re-dissolved within a time period before the next driving. On the other hand, when the drive frequency increases, the stability of ejection may decrease due to insufficient recovery from the dissolution. However, for ejecting a large amount of the solution effectively, the ejection should be carried out at a higher frequency of not less than a predetermined level. In the present invention, the drive frequency is preferably in the range of 0.1 kHz to 100 kHz, and more preferably in the range of 1 kHz to 30 kHz.

In the case of using the ejection liquid of the present invention for producing biochips and biosensors, it is possible to use substantially the same system as that of inkjet printers commercially available presently.

On the other hand, it is preferable that the liquid ejection apparatus of the present invention include a thermal inject head capable of ejecting fine liquid droplets of the ejection liquid by the thermal inkjet system and that a number of ejection units which constitute the head are constructed so that they can be driven independently of each other. At that time, it is preferable to adopt a liquid ejection cartridge of an integrated configuration such that wires which connect electrical connection parts serving for connection of a plurality of control signals or the like required for independently drive respective ejection units and the respective ejection units are integrated and a tank for storing the ejection liquid and the ejection head having the electrothermal conversion element that provides thermal energy to the ejection liquid are integrated.

Next, description is made by taking as an example the case where the ejection liquid according to the present invention is used for atomization, in particular for an inhaler. As the inhaler, it is preferable to use an inhaler which has a part for converting an ejection liquid (liquid formulation) to fine liquid droplets and a part for incorporating the atomized fine liquid droplets into a carrier airflow, independently of each other. In this way, by separating the atomizing part which converts the liquid into fine liquid droplets from the part in which the airflow containing the fine liquid droplets is formed, the amount of ejection can be uniformly adjusted. In other words, the amount of a protein and/or a peptide as effective components in the airflow, that is a predetermined dose per single administration, can be adjusted more uniformly when allowing an administration object to inhale the airflow. Also, by composing an ejection head in such a way that a plurality of ejection units each having a number of ejection orifices is provided so as to eject different effective components for every unit, the ejection amounts of a plurality of effective components can be controlled independently of each other.

Further, by utilizing an ejection head based on the thermal inkjet principle that allows disposition of ejection orifices at a high density per unit area as an atomizing mechanism, the size of an inhaler can be so reduced as to allow a user to bring it with him.

In the inhaler for pulmonary inhalation, it is important that the particle size distribution of liquid droplets contained in airflow is 1 to 5 μm and the range of particle size is narrow. Further, when it is utilized as a portable apparatus, the constitution of the apparatus needs to be compact.

FIG. 1 is a schematic view illustrating an example of a liquid ejection cartridge with such an inhaler. The liquid ejection cartridge is composed as a head cartridge unit in which in a casing 1, a head part 4, a tank 2 for storing an ejection liquid, a liquid path 3 for supplying the liquid from the tank 2 to the head part 4, an electric connection part 6 for exchange of a drive signal or a control signal with a controller for driving each liquid ejection unit of the head part 4, and an inner wire 5 for the head part 4 and the electric connection part 6 are formed integrally. The head cartridge may be composed so as to be attachable to and detachable from the inhaler as needed. As the head part 4, one having the constitution of the liquid droplet ejection head described in Japanese Patent Application Laid-Open No. 2003-154665 is suitably used.

An example of a portable inhaler having a head cartridge unit composed in such a way will be described referring to FIGS. 2 and 3. The inhaler shown in FIGS. 2 and 3 has a constitution as an example which is designed to be compact such that a user can bring with him or her as a portable inhaler for a medical purpose.

FIG. 2 is a perspective view illustrating the appearance of the inhaler. In the inhaler, a housing is formed by an inhaler main body 10 and an access cover 7. In the housing, a controller, an electric source (battery) (not shown), and the like are housed. FIG. 3 is a perspective view illustrating a state in which the access cover 7 is opened. When the access cover 7 is opened, a connection part between a head cartridge unit 12 and a mouthpiece 8 (ejection orifice) can be seen. Air is sucked into the inhaler from an air intake port 11 by the inhalation operation of a user and guided to enter the mouthpiece 8 and is then mixed with liquid droplets ejected from the orifice provided in the head part 4 of the head cartridge unit 12, thereby forming a mixed airflow. The mixed air flow moves to a mouthpiece exit having such a shape that a person can put it in his mouth. By putting the tip of the mouthpiece 8 into the mouth and holding it between the teeth and then breathing in, the user can inhale efficiently the liquid droplets ejected from the liquid ejection part and induced to the mouthpiece 8.

Incidentally, the head cartridge unit 12 may be composed so as to be attachable to and detachable from the inhaler as needed.

By adopting the constitution as shown in FIGS. 2 and 3, the fine liquid droplets formed can naturally be delivered into the throat and trachea of an administration object with an inspiration. Thus, the amount of atomized liquid (administration amount of effective component) is not dependent on the various volume of inspired air but is controllable independently.

EXAMPLES 1 TO 4 AND COMPARATIVE EXAMPLES 1 TO 8

The present invention will be described below in more detail with reference to examples but not limited by these particular examples. Here, "%" means % by weight.

The procedure for preparing an insulin solution will be described below. An appropriate amount of insulin (manufactured by Sigma-Aldrich Corporation) was dissolved in 0.01 M HCl aqueous solution and then added with 50 mg/ml of an aqueous citric acid solution adjusted to pH 7 with 2 M NaOH to be a predetermined concentration while stirring. After that, the mixture was adjusted to pH 7 by 0.1 M NaOH, followed by dissolving by the additional of water so that the predetermined concentration of an insulin was obtained.

Insulin aspart and insulin lispro solutions were added with 50 mg/ml of an aqueous citric acid solution adjusted to pH 7.4 with 2 M NaOH to be a predetermined concentration while being stirred with NovoRapid (manufactured by Novo Nordisk Co., Ltd.) and Humalog (manufactured by Eli Lilly). After that, the mixture was dissolved by the addition of water so that the predetermined concentrations of insulin aspart and insulin lispro were obtained.

An ejection head of an inkjet printer (trade name: PIXUS 950i; manufactured by CANON Inc.) was filled with an ejection liquid prepared by the procedure as described above. The ejection head was driven by an ejection controller to evaluate the ejection property at a frequency of 24 kHz. The continuous ejection for 10 minutes was evaluated as A, and the ejection stopped within less than 10 minutes was evaluated as C. As each of Comparative Examples 1 to 8, an ejection liquid was prepared by adding a compound other than citric acid to an insulins solution and then was subjected to the liquid droplet ejection experiments carried out in the same manner as Examples 1 to 4. The formulations and the ejection evaluation that were examined in the Examples 1 to 4 and Comparative Examples 1 to 8 are collectively shown in Table 1. Here, the "unit" for the concentrations of insulins used in Table 1 is the unit of a given dose commonly used for insulins on an international basis.

TABLE 1

| | Insulins | Insulins Conc. | Additive for improving ejection property | Conc. of additive for improving ejection property | Ejection property |
|---|---|---|---|---|---|
| Example 1 | Insulin | 2.0 mg/mL | Citric acid | 0.1 mg/mL | A |
| Example 2 | Insulin | 10.0 mg/mL | Citric acid | 1.0 mg/mL | A |
| Example 3 | Insulin aspart | 80 unit/mL | Citric acid | 1.0 mg/mL | A |
| Example 4 | Insulin lispro | 80 unit/mL | Citric acid | 1.0 mg/mL | A |
| Comparative Example 1 | Insulin | 2.0 mg/ml | Absence | — | C |
| Comparative Example 2 | Insulin | 2.0 mg/ml | Tween80 | 1.0 mg/mL | C |
| Comparative Example 3 | Insulin | 2.0 mg/ml | Glycerine | 10.0 mg/mL | C |
| Comparative | Insulin | 10.0 mg/ml | PEG4000 + Tween80 | 60.0 mg/mL + | C |

TABLE 1-continued

|  | Insulins | Insulins Conc. | Additive for improving ejection property | Conc. of additive for improving ejection property | Ejection property |
|---|---|---|---|---|---|
| Example 4 |  |  |  | 1.0 mg/mL |  |
| Comparative Example 5 | Insulin aspart | 80 unit/mL | Absence | — | C |
| Comparative Example 6 | Insulin aspart | 80 unit/mL | Tween80 | 1.0 mg/mL | C |
| Comparative Example 7 | Insulin lispro | 80 unit/mL | Absence | — | C |
| Comparative Example 8 | Insulin lispro | 80 unit/mL | Tween80 | 1.0 mg/mL | C |

Each of the ejection liquids of Examples 1 to 4 was subjected to a HPLC analysis under predetermined measurement conditions (Equipment: JASCO Corporation; Column: YMC-Pack Diol-200, 500×8.0 mm TD; Eluent: 0.1 M KH2PO4-K2HPO4 (pH 7.0) containing 0.2M NaCl; Flow rate: 0.7 ml/min; Temperature: 25° C.; Detection: UV at 215 nm) before and after the ejection to confirm the change in the composition of the ejection liquid. As a result of the HPLC analysis, in Examples 1 to 4, no change was observed in the peak position and peak area and in the liquid composition before and after the ejections.

EXAMPLES 5 TO 8 AND COMPARATIVE EXAMPLES 9 TO 16

On the other hand, a liquid ejection head according to the thermal inkjet system having a nozzle diameter of 3 μm was prepared, and a tank connected thereto was filled with a 30% ethanol aqueous solution. The liquid ejection head was driven by a controller electrically connected thereto to eject the liquid from the ejection orifice, and the particle diameter and particle size distribution of the obtained liquid droplets (mist) were measured and confirmed with a laser diffraction particle size analyzer (Spraytech, manufactured by Malvern Instruments Ltd). As a result, the liquid droplets having a sharp particle distribution peak at about 3 μm were detected.

The tank connected to the liquid ejection head having the nozzle with a diameter of 3 μm was filled with the ejection liquid prepared by the procedure described above, and the ejection head was driven by the ejection controller to carry out ejection at a frequency of 20 kHz and a voltage of 12 V for 1 second (first ejection). Further, after an interval of 3 seconds, the next 1-second ejection (second ejection) was carried out. This operation was repeated 50 times and the continuity of the ejections was confirmed by visual observation. The ejection continuity was evaluated: as A, when liquid droplets were ejected 50 times or more; as B, when the liquid droplet ejection stopped within the range between 15 times to 50 times; and as C, when the liquid droplet ejection stopped with operations of less than 15 times. Also, each ejection liquid was subjected to a HPLC analysis with respect to the ejection liquid predetermined measurement conditions before and after the ejection to confirm the change in the composition of the ejection liquid.

As Comparative Examples 9 to 16, ejection liquids, in which a compound other than citric acid was added to an insulins solution, were prepared. Subsequently, the liquid droplet ejection experiments were carried out in the same manner as Examples 5 to 8. The formulations and the ejection evaluation that were examined in the Examples 5 to 8 and Comparative Examples 9 to 16 are collectively shown in Table 2 below.

TABLE 2

| | Insulins | Insulins Conc. | Additive for improving ejection property | Conc. of additive for improving ejection property | Ejection property |
|---|---|---|---|---|---|
| Example 5 | Insulin | 2.0 mg/mL | Citric acid | 1.0 mg/mL | A |
| Example 6 | Insulin | 10.0 mg/mL | Citric acid | 1.0 mg/mL | A |
| Example 7 | Insulin aspart | 80 unit/mL | Citric acid | 1.0 mg/mL | A |
| Example 8 | Insulin lispro | 80 unit/mL | Citric acid | 1.0 mg/mL | A |
| Comparative Example 9 | Insulin | 2.0 mg/ml | Absence | — | C |
| Comparative Example 10 | Insulin | 2.0 mg/ml | Tween80 | 1.0 mg/mL | C |
| Comparative Example 11 | Insulin | 2.0 mg/ml | Glycerine | 10.0 mg/mL | C |
| Comparative Example 12 | Insulin | 10.0 mg/ml | PEG4000 + Tween80 | 60.0 mg/mL + 1.0 mg/mL | C |
| Comparative Example 13 | Insulin aspart | 80 unit/mL | Absence | — | C |
| Comparative Example 14 | Insulin aspart | 80 unit/mL | Tween80 | 1.0 mg/mL | C |
| Comparative Example 15 | Insulin lispro | 80 unit/mL | Absence | — | C |
| Comparative Example 16 | Insulin lispro | 80 unit/mL | Tween80 | 1.0 mg/mL | C |

No ejection from the thermal inkjet head having a nozzle diameter of 3 μm was observed in each of Comparative Examples 9 to 16. In contrast, a stable ejection was observed in each of Examples 5 to 8, thereby confirming additional effects of the compounds of the present invention. The results of the HPLC analyses performed for Examples 5 to 8 indicated that no change was observed in the peak position and peak area, and in the liquid composition before and after the ejections.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2004-279864, filed Sep. 27, 2004, No. 2005-252154, filed Aug. 31, 2005, and No. 2007-001179, filed Jan. 9, 2007, which are hereby incorporated by reference herein in their entirety.

What is claimed is:

1. A method for ejecting an insulin-containing liquid comprising:
   providing a liquid comprising (a) at least one kind of insulin and (b) citric acid; and
   ejecting the liquid by a thermal inkjet system,
   wherein content of the at least one kind of insulin in the liquid to be ejected is 1 μg/ml to 200 mg/ml,
   wherein content of the citric acid in the liquid to be ejected is 1 μg/ml to 2.0 g/ml, and
   wherein a drive frequency of the thermal inkjet system is in the range of 0.1 kHz to 100 kHz,
   whereby when the drive frequency is 24 kHz, continuous ejection for at least ten minutes may be achieved.

2. The method according to claim 1, wherein content of the at least one kind of insulin in the liquid to be ejected is 0.1 mg/ml to 60 mg/ml.

3. The method according to claim 1, wherein the content of the citric acid in the liquid to be ejected is 10 μg/ml to 200 mg/ml.

4. The method according to claim 1, wherein the drive frequency is in the range of 1 kHz to 30 kHz.

5. The method according to claim 1, wherein the liquid further comprises a surfactant.

6. The method according to claim 5, wherein the liquid further comprises a water-soluble organic solvent in an amount of 1 to 30% by weight with respect to the weight of the liquid.

7. The method according to claim 6, wherein the at least one kind of insulin comprises an insulin modified by PEG or PVA.

* * * * *